(12) United States Patent
Widen

(10) Patent No.: US 8,282,393 B2
(45) Date of Patent: Oct. 9, 2012

(54) SYSTEM AND METHOD FOR REMOVING SURFACE CONTAMINATION

(76) Inventor: Randy Miles Widen, Lusby, MD (US)

( * ) Notice: Subject to any disclaimer, the term of this patent is extended or adjusted under 35 U.S.C. 154(b) by 103 days.

(21) Appl. No.: 12/798,595

(22) Filed: Apr. 7, 2010

(65) Prior Publication Data

US 2010/0261132 A1    Oct. 14, 2010

Related U.S. Application Data

(60) Provisional application No. 61/212,213, filed on Apr. 8, 2009.

(51) Int. Cl.
*B08B 3/00* (2006.01)
*B60R 1/06* (2006.01)

(52) U.S. Cl. ............ 433/31; 134/102.1; 134/102.2; 359/509; 359/882

(58) Field of Classification Search .......... 433/30, 433/31, 80, 29, 141; 600/189, 246, 247, 600/248; 359/871, 881, 882, 509, 838, 845; 134/102.1, 102.2, 104.1, 166, 171, 94.1, 134/99.1, 100.1, 115 R, 182, 198; 239/423, 239/433, 502, 507, 509, 510, 512, 520, 521, 239/523, 524
See application file for complete search history.

(56) References Cited

U.S. PATENT DOCUMENTS

| | | | | |
|---|---|---|---|---|
| 3,027,644 A | * | 4/1962 | Piscitelli | 433/30 |
| 3,048,924 A | * | 8/1962 | Whitman et al. | 433/30 |
| 3,052,031 A | * | 9/1962 | Piscitelli | 433/30 |
| 3,091,034 A | * | 5/1963 | Piscitelli | 433/30 |
| 3,755,903 A | * | 9/1973 | Spinello | 433/30 |
| 3,969,824 A | | 7/1976 | Widen et al. | |
| 3,986,266 A | * | 10/1976 | Vellender | 433/30 |
| 4,279,500 A | * | 7/1981 | Kondo et al. | 399/346 |
| 4,279,594 A | * | 7/1981 | Rigutto | 433/31 |
| 4,512,635 A | | 4/1985 | Melde | |
| 5,622,492 A | | 4/1997 | Eli | |
| 5,951,284 A | | 9/1999 | Lake | |
| 6,296,694 B1 | * | 10/2001 | Miller | 106/13 |
| 6,443,729 B1 | | 9/2002 | Watson | |
| 6,932,601 B2 | | 8/2005 | Frider et al. | |
| 7,021,798 B2 | | 4/2006 | Tsimerman et al. | |

* cited by examiner

*Primary Examiner* — Cris L Rodriguez
*Assistant Examiner* — Justin O'Donnell
(74) *Attorney, Agent, or Firm* — Ryndak & Suri LLP

(57) ABSTRACT

A system and method are provided in which a laminar flow of pressurized gas from a curved slit in a chamber is directed across a surface to propel a laminar flow of a liquid, below the laminar flow gas, across the surface to prevent surface contamination or remove contaminants from the surface. In a particular application, the system and method are employed in a self-cleaning dental mirror tool including a dental mirror attached to a handle, wherein the gas is air, the liquid is water, and the surface is the reflective surface of the dental mirror.

13 Claims, 6 Drawing Sheets

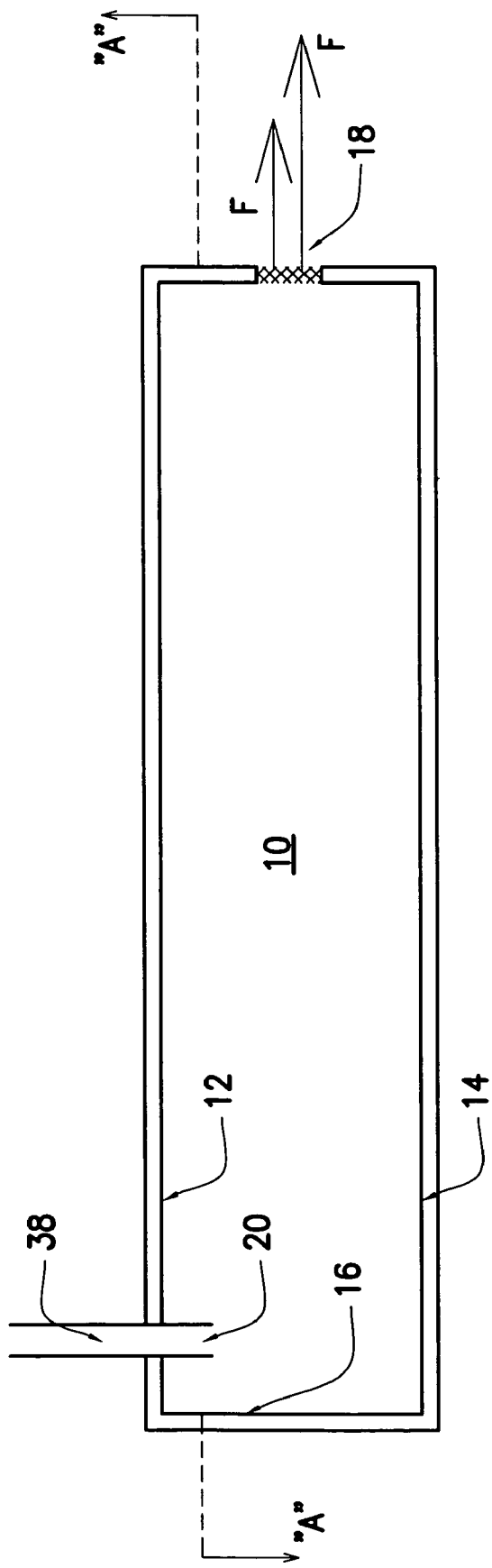

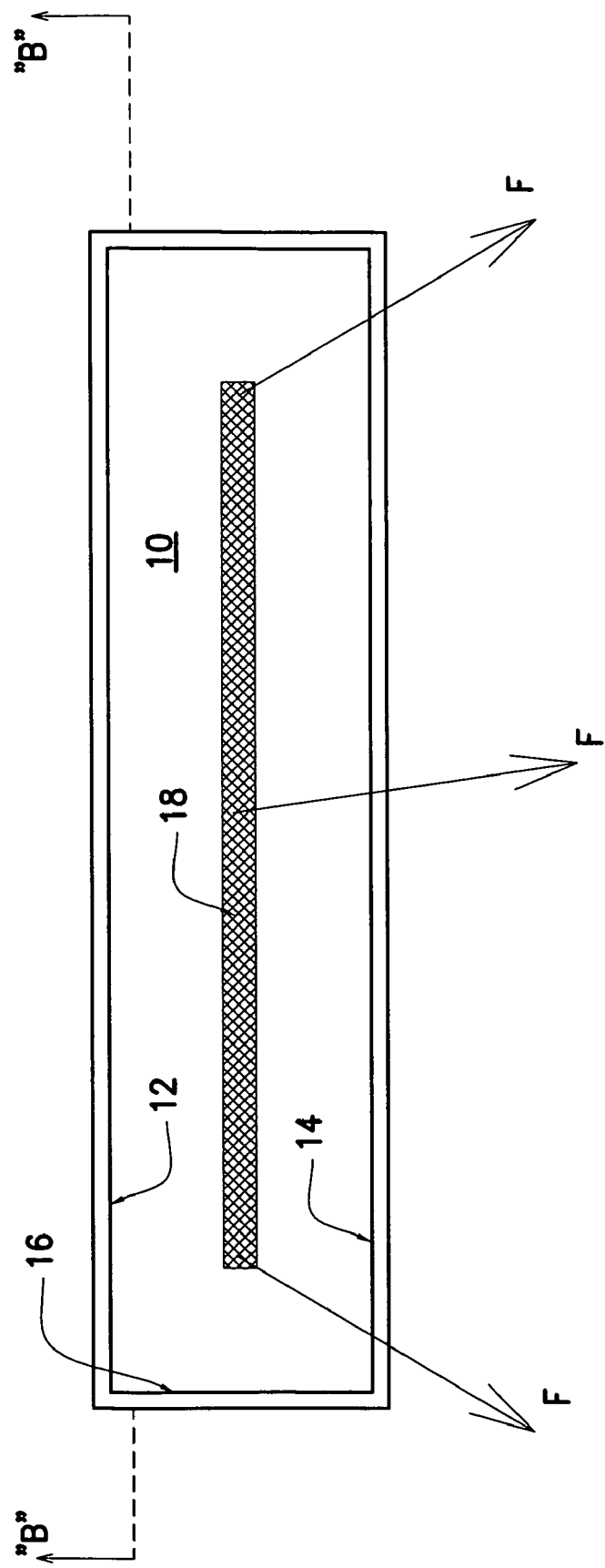

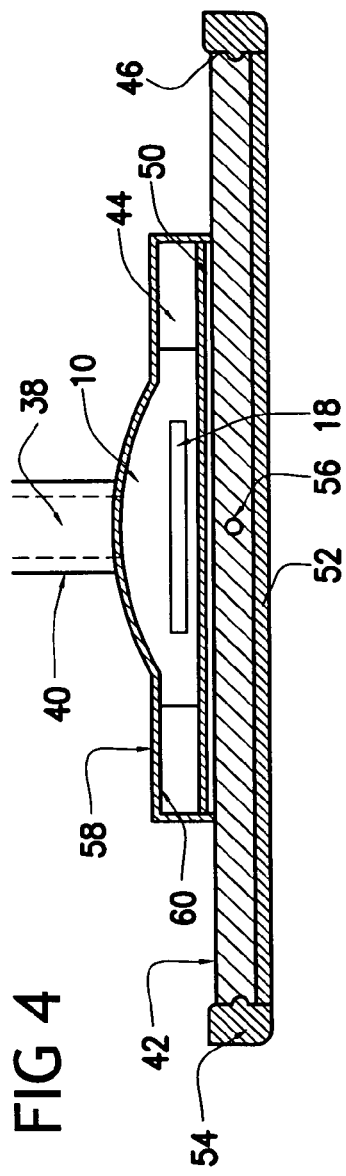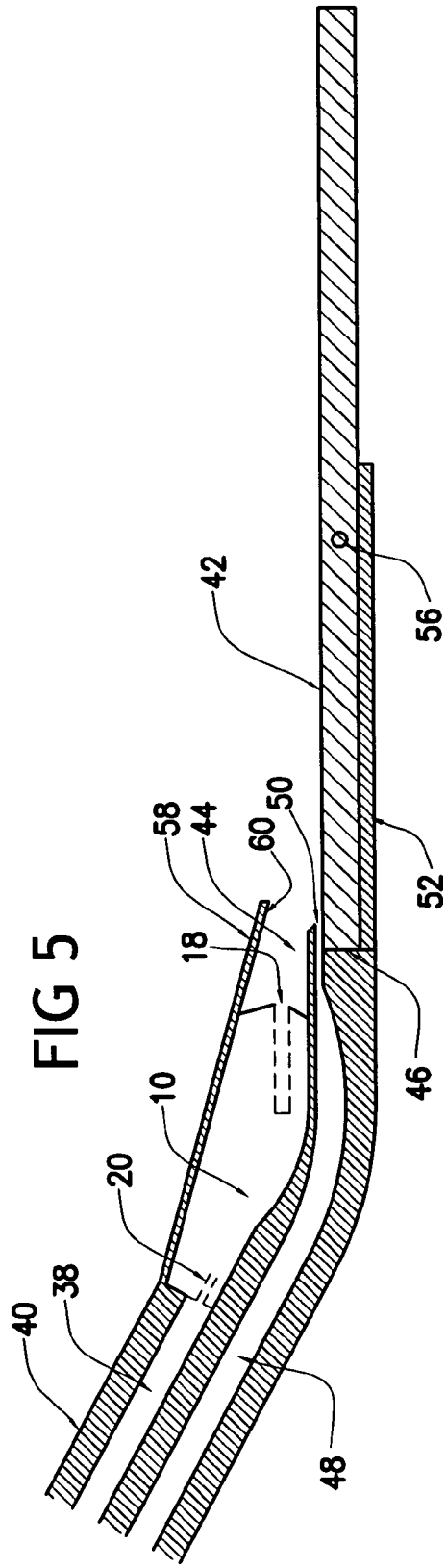

SYSTEM AND METHOD FOR REMOVING SURFACE CONTAMINATION

CROSS-REFERENCE TO RELATED APPLICATIONS

This application claims the benefit of U.S. Provisional Application No. 61/212,213, filed Apr. 8, 2009, the disclosure of which is hereby incorporated in its entirety.

FIELD OF THE INVENTION

The present invention relates generally to an improved system and method for removing surface contamination. More particularly, the system and method of the invention prevent the formation of, or remove, coatings of debris on a surface that interfere with the use of the surface. The invention is particularly useful for the prevention and removal of biofilms, i.e., organic debris and moisture found on a surface during use if not removed. One illustrative example of an application for the invention is dental instruments and more particularly an improved self-cleaning hand dental mirror.

BACKGROUND OF THE INVENTION

Many surfaces become contaminated during use with debris or other materials which inhibit use of the surface. In particular, many surfaces develop during use a coating or film of organic debris and moisture, sometimes referred to herein as a "biofilm." It is typically necessary to remove the biofilm manually during use to permit use to continue. Often it is necessary to repeat the removal procedure periodically, interfering with and making use difficult and inefficient.

As an example of a surface suitable for application of the invention, dentists commonly use hand-held dental mirrors to enable them to clearly see areas inside a patient's mouth while performing a procedure such as drilling in or on a tooth. During use, the reflective surface of the mirror quickly becomes obscured from spray from the high-speed dental drill, dental material and tooth debris, fog, mist, etc. This impaired reflective surface can lead to reduced workmanship in dental procedures unless the mirror is continually cleaned and/or a surface tension reducer is constantly applied. It has therefore been customary for dentists to frequently remove the dental mirror from a patient's mouth, clean the mirror surface, and reposition the mirror in the patient's mouth. This is both inconvenient and inefficient.

Other surfaces which may develop biofilms or other coatings of contaminants which may advantageously be prevented or removed by the system and method of the invention include, but are not limited to, windows on buildings (especially high-rise buildings); lenses and windows on satellites and spacecraft; windows and windshields on vehicles such as airplanes; glass shower enclosures; mirrors; cooking surfaces; surfaces from which removal of biofilms will facilitate fluid flow, such as surfaces of pipes, ducts and membranes; glass or plastic aquarium surfaces (e.g., to prevent or remove algae growth); tank surfaces; various other glass or mirror surfaces; and surgical sites where there is debris in the field. The foregoing list is illustrative only and is not intended to limit the scope of the invention or its potential applications.

It is desirable to provide a system and method to prevent or inhibit the formation of biofilms or other coatings of contaminants on surfaces. It is also desirable to provide a system and method to remove biofilms or other coatings of contaminants which have formed on surfaces. It is also desirable to prevent and remove biofilms or other coatings of contaminants during use of the surface without interfering with the use or requiring manual or other action by the user which might require interruption of the use.

SUMMARY OF THE INVENTION

In accordance with one aspect of the present invention, a system for preventing or removing biofilms or other coatings of contaminants on a surface comprises an apparatus including a substantially enclosed gas pressurization chamber. Where the surface to be cleaned defines a horizontal plane, the chamber includes a generally vertical face extent with a horizontally curved profile, a gas inlet orifice to allow gas under pressure to pressurize the chamber, and a gas outlet orifice in the curved face extent configured so that gas flows from the chamber in divergent directions normal to the gas outlet orifice, thus creating a spreading laminar flow of gas capable of flowing across substantially an entire surface that is wider than the orifice itself. A liquid conduit including a liquid outlet orifice is also provided, the liquid outlet orifice located below the laminar gas flow so that the laminar gas flow propels the layer of liquid in a laminar flow across the surface. Preferably, the liquid outlet orifice is located downstream of the gas outlet orifice so that the laminar gas flow flows over the liquid as it exits the liquid outlet orifice.

In one embodiment of the invention, the apparatus is incorporated into a self-cleaning dental mirror tool. In the tool, the surface to be cleaned is the reflective surface of a mirror. The liquid outlet orifice is disposed proximate to one edge of the mirror surface for dispensing a thin layer of a liquid onto the mirror surface. The gas outlet orifice is disposed above the liquid outlet orifice for simultaneously dispensing a thin laminar layer of gas across and parallel to the mirror surface at a pressure greater than that of the layer of liquid. Optionally but advantageously, a gas conduit for providing gas to the chamber and the liquid conduit are located in a handle of the tool.

In another embodiment, the gas outlet orifice is a slit formed in the face extent so that the top and bottom of the slit are spaced apart at least substantially vertically, and in this manner the laminar gas flow passes through the slit at least substantially horizontally, in a direction normal to the slit, and the slit has an at least substantially uniform height. Advantageously, the slit has a vertical height of from about 5% to about 20% of the vertical height of the chamber.

In another aspect, the invention provides a method for preventing or removing biofilms or other coatings of contaminants on a surface. The method includes providing an apparatus substantially as described, flowing a gas into the chamber so that a pressurized, laminar flow of gas flows from the chamber in a direction normal to the gas outlet orifice, and flowing a liquid from the liquid conduit through the liquid outlet orifice onto the surface so that the laminar gas flow propels the liquid in a laminar liquid flow across the surface. Advantageously, the liquid may be water, and the gas may be air. Optionally, but preferably, a surface tension reducer may be mixed into the stream of liquid upstream of the liquid outlet orifice, to reduce turbulence in the liquid flow (i.e., to make the liquid flow more laminar) and thus to increase visibility through the liquid flow.

BRIEF DESCRIPTION OF THE DRAWINGS

FIG. 1 is a cross-sectional view of a circular chamber for producing normal, laminar fluid flow across a surface in accordance with the invention.

FIG. 1*a* is cross-sectional view of the chamber of FIG. 1 taken along line A-A.

FIG. 1b is a cross-sectional view of the chamber of FIG. 1 taken along line B-B showing the orifice.

FIG. 4 is a cross-sectional view of the dental mirror of FIG. 3 taken along line 4-4.

FIG. 5 is a longitudinal section view taken along line 5-5 of FIG. 3.

DETAILED DESCRIPTION OF THE INVENTION

It is known in the art to use a flow of fluid, for example, air and/or water, to clear a surface of debris. An example of a device using this method is the dental mirror disclosed in applicant's U.S. Pat. No. 3,969,824, the disclosure of which is incorporated herein in its entirety by reference. The device disclosed in the earlier patent attempts to disperse the air flow coming down the handle/center air conduit by having the air hit a stationary obstruction that is air foil shaped, being thickest in the center and tapering toward the periphery.

Rather than using an airfoil-shaped obstruction in the fluid stream, the present invention disperses air using an entrapment chamber wherein the air is further pressurized. It has been found that the air chamber of the present invention allows more control of the air flow than the air foil. The aerodynamic flow lines are more predictable using a chamber than when using an airfoil. Design considerations with a chamber are easier to anticipate, and the chamber design is easier and less expensive to fabricate. The dispersion effect is created by opening a slit in a curved face of this chamber, the slit and chamber being configured such that the air will disperse radially through the curved slit from the pressurized chamber. With sufficient pressure in the chamber, pressure being substantially uniform within the chamber behind the slit, the flow from the slit will be radial (i.e., normal) to the arc extent of the slit. The slit is horizontal and uniform in vertical dimension with respect to the roof and floor of the chamber. In order to build up pressure within the chamber, the slit must be relatively thin in relation to the height of the chamber or else the air will flow "straight" from the chamber. This slit height is to be determined by the amount of pressure in the chamber and the desired velocity of the escapement flow. This escapement flow is preferably approximately 25-50 feet per second, laminar, non turbulent and radial (i.e., normal) to the slit's arc extent.

This dispersion technique does not create laminar flow by using the gradual air foil shaped obstruction to simply guide the air flow from a center flow by "squeezing" it to the maximum in the center and gradually releasing it through an effectively wider space. Instead, air is pressurized upstream from the surface by using a "holding chamber" and curved outlet orifice versus merely deflecting flow from an inlet orifice with a tapering air foil shaped obstruction.

Figure 1:
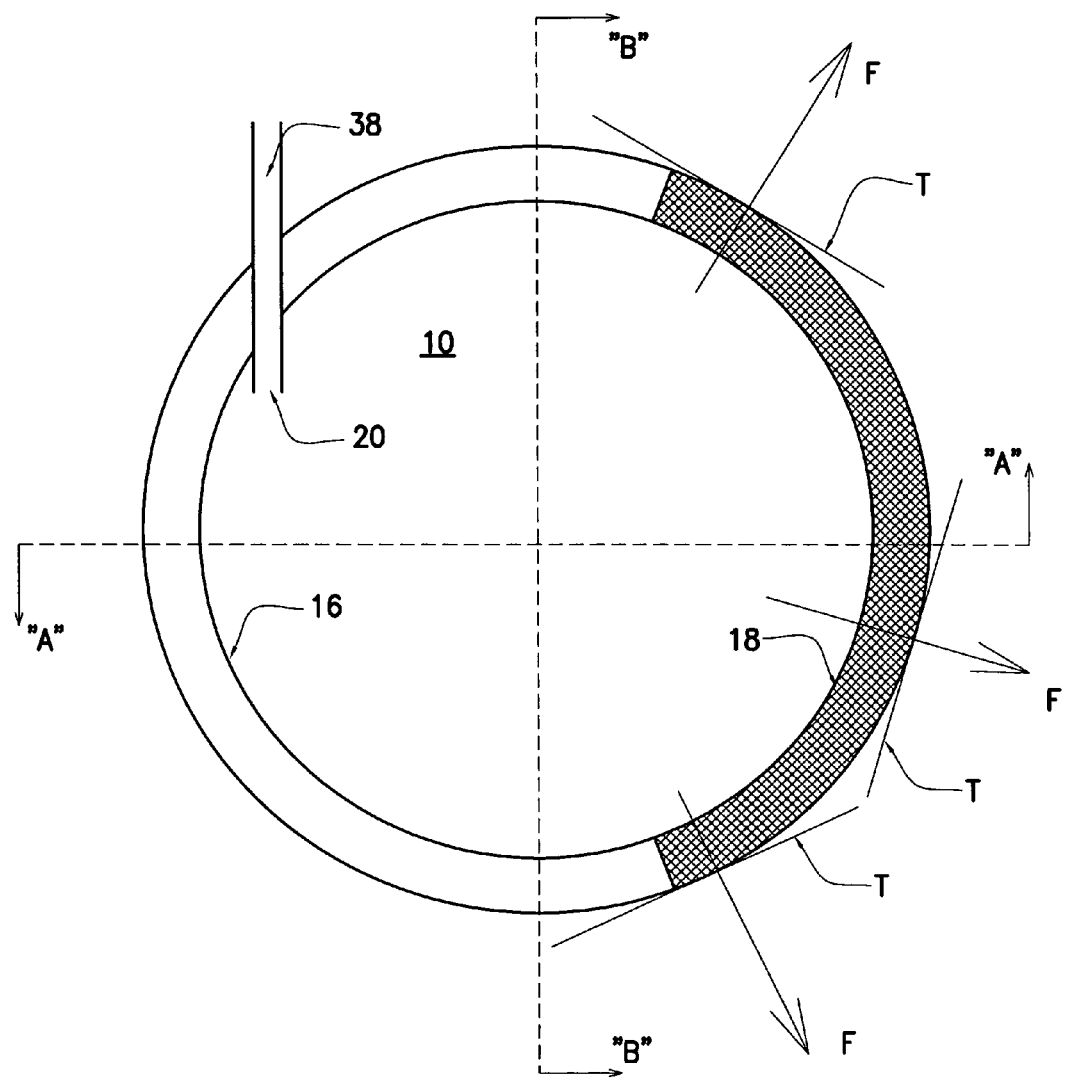

As shown in FIGS. 1, 1a, and 1b, a circular gas pressurization chamber 10 has a ceiling 12, floor 14 and sides 16 and is approximately the shape of a horizontal cylinder segment. For use in a dental mirror tool, the approximate linear and cubic dimensions of the chamber are comparable to that of an aspirin tablet, or about ⅜ inch diameter×⅛ inch height. A gas outlet orifice 18 is provided along approximately 90 to 120 degrees of the chamber's circumference.

As shown in FIGS. 1a and 1b, gas outlet orifice 18 is located generally opposite an air inlet 20 in chamber 10, and in the side wall 16 of chamber 10 adjacent to floor 14 of chamber 10. Although not shown, floor 14 of chamber 10 will be positioned adjacent the surface to be cleaned. Orifice 18 preferably has a vertical height approximately 5% to 20% of the vertical height of chamber 10 (i.e., of the height of side 16).

A suitable gas (air will be used as an example) enters inlet 20 under pressure and pressurizes chamber 10. Air exits chamber 10 through outlet orifice 18 such that the outlet flow "F" is laminar and perpendicular to the tangent "T" to the radius at any point along orifice 18 as shown. In other words, the flow "F" created will be radial to the orifice's arc extent and laminar to the surface over which it flows. The pressure in chamber 10 should be such that air flows from outlet orifice 18 at a pressure greater than ambient pressure.

Figure 2:
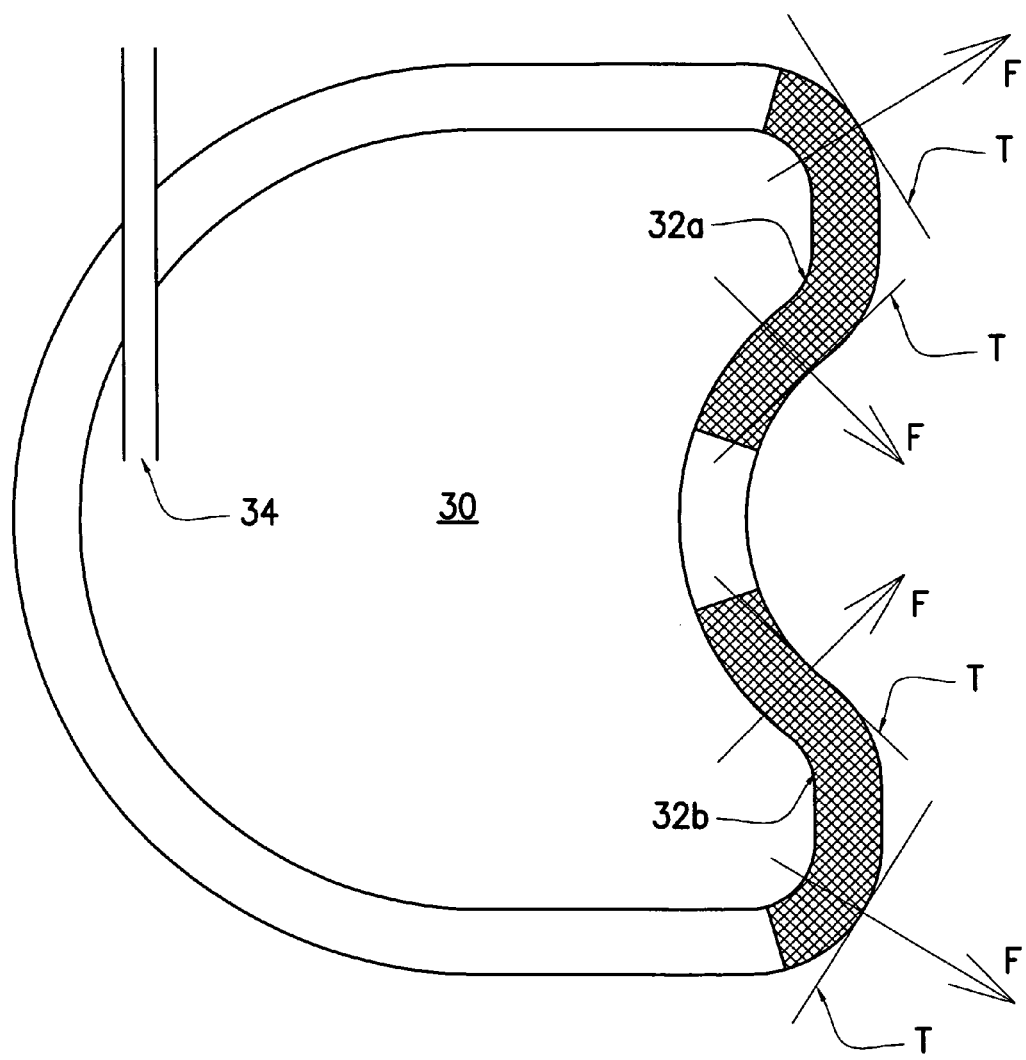
FIG. 2 is a top plan view of an alternate chamber suitable for use with the invention.

A top plan view of an alternate chamber 30 is shown in FIG. 2. The radial flow lines "F" are created and laminar flow exits chamber 30 across the surface to be cleaned (not shown). In this embodiment, chamber 30 is not circular but has a shape generally as shown in FIG. 2. Two gas outlet orifices 32a, 32b are provided, generally opposite an air inlet 34, and arranged to direct air flow "F" in a direction perpendicular to orifice tangents "T" as shown, across the surface to be cleaned.

Generally, in a system for preventing and removing surface contamination incorporating an air chamber according to the invention as just described, liquid such as water is introduced to the surface to be cleaned through a liquid outlet orifice downstream of gas outlet orifice 18 or gas outlet orifices 32a, 32b of chamber 10 or 30, respectively. The air flow draws the liquid across the surface to be cleaned, which may for example be a mirror surface.

Figure 3:
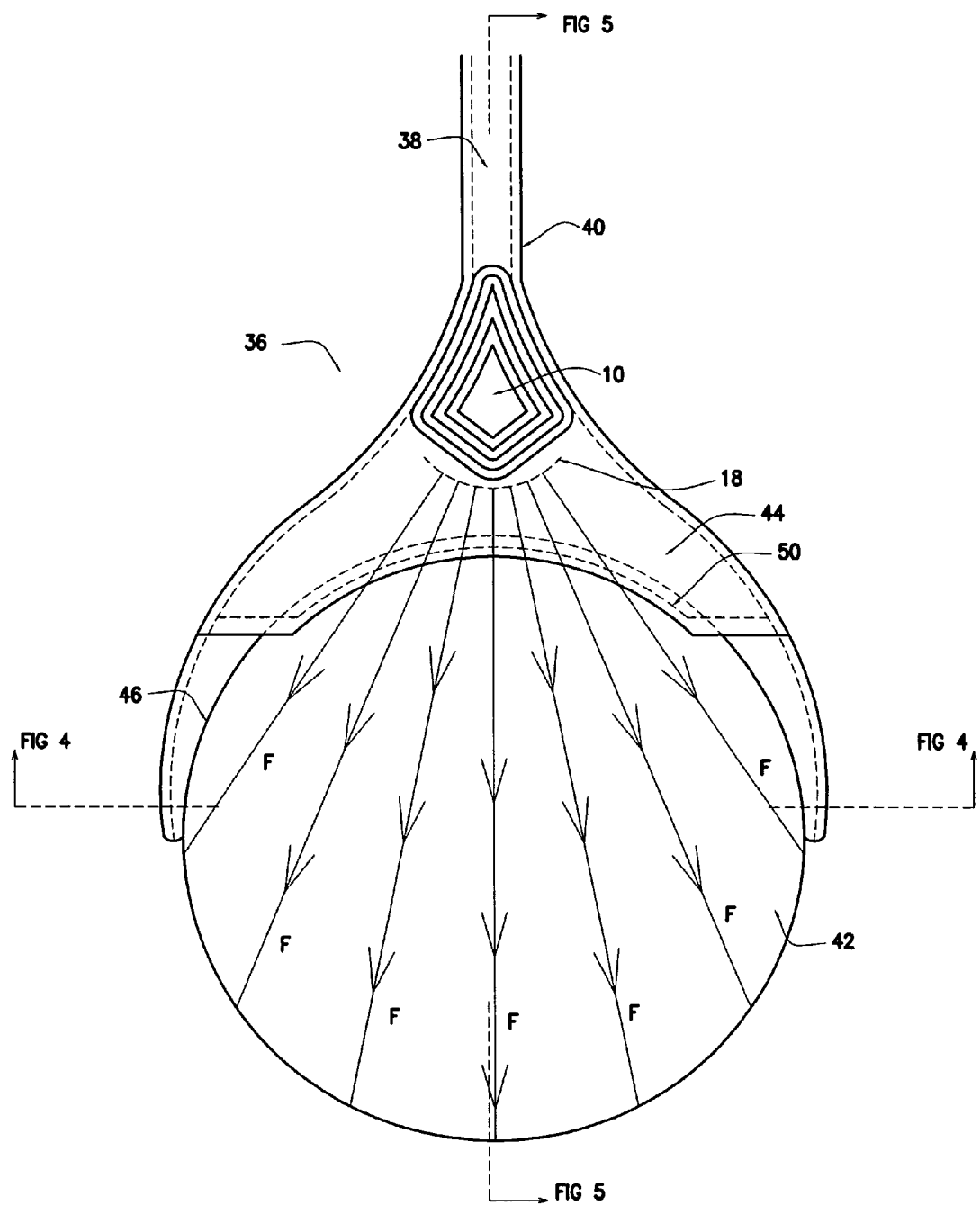
FIG. 3 is a partial plan view of a dental mirror in accordance with the invention.

As an example of a system according to the invention for preventing and removing surface contamination, dental mirror tool 36 incorporating air chamber 10 according to the invention is shown in FIGS. 3 through 5. Pressurized air from an air conduit 38 in a handle 40 of mirror tool 36 enters air chamber 10 through inlet orifice 20. Air chamber 10 is upstream of and proximal to a mirror surface 42 of mirror tool 36. To protect gas outlet orifice 18, for example from debris or impacts, chamber 10 may advantageously be located in a flange cavity 44 between handle air conduit 38 and an edge 46 of mirror surface 42. Air chamber outlet 18 will dispense air through flange cavity 44 to mirror surface 42. A liquid such as water is provided from a liquid conduit 48 in handle 40 and exits through a liquid outlet orifice 50 onto mirror surface 42. Mirror tool 36 includes other structural elements as shown, including mirror holding bottom plate 52, mirror holding outer frame 54, mirror holding detent 56, flange top surface 58 and flange inner surface 60.

Pressurized air traversing laminar flow vectors "F," perpendicular to the tangent "T" of a radial chord along air chamber outlet orifice 18, propels in a fluid-dynamic manner, by pressure differential and/or entrapment, water from liquid outlet orifice 50. Water flow is laminar across mirror surface 42 and follows the gas flow lines F in FIGS. 1-3, as the water flow is propelled by the gas flow. Optionally, but preferably, these effects can be enhanced by introducing a surface tension reducer into the stream of water or other suitable liquid upstream of liquid outlet orifice 50, which will reduce turbulence in the liquid flow (i.e., make the flow even more laminar) and thus increase visibility of the mirror surface through the liquid flow. For example, the present inventor has found that placing a cartridge of Polyox™ water soluble resin, available from the Dow Chemical Company, in-line with the liquid flow upstream of the handle, so that the surface tension reducer is dissolved into the stream of liquid at a metered rate, effectively improves the laminar quality of the flow of liquid across the mirror surface.

Generally speaking, the invention utilizes an enclosed chamber with a curved face extent, an inlet orifice to allow gas under pressure to pressurize the chamber, and an outlet orifice in the curved face extent so that gas flows from the chamber perpendicular to the tangent of the radius of the orifice in the curved face extent. In the context of a self cleaning dental mirror, the apparatus comprises in combination: a mirror surface; a first orifice disposed along one edge of the mirror surface for dispensing a thin layer of a liquid onto the surface; and a second orifice disposed above the first orifice for simultaneously dispensing a thin laminar layer of gas flow across and parallel to the mirror surface, the laminar gas flow propelling a laminar flow of the liquid beneath the laminar gas flow.

Although the invention has been described by reference to one illustrative embodiment, a dental mirror, it will be understood that the invention can be adapted through appropriate choices of dimensions and configurations for use in a wide variety of other applications, including those mentioned herein and others that will be apparent. The shape of the chamber, dimensions of the gas outlet orifice, internal chamber pressure and other design parameters are appropriately selected to so that the liquid is "picked up" by the laminar air flow to create laminar liquid flow across the surface to be cleaned. A device in accordance with the invention will effectively clean the surface and, in the case of a glass or mirror surface, provide a clear, unobstructed, non-distorted view therethrough or therein using a laminar "air curtain" to draw a laminar flow of liquid across the surface.

While the invention has been described with respect to certain preferred embodiments, as will be appreciated by those skilled in the art, it is to be understood that the invention is capable of numerous changes, modifications and rearrangements, and such changes, modifications and rearrangements are intended to be covered by the following claims.

What is claimed is:

1. An apparatus for providing a laminar flow of liquid across a surface to remove contamination from the surface, comprising:
   a gas conduit;
   a substantially enclosed gas pressurization chamber having a curved face extent, a gas inlet orifice connected to the gas conduit to allow gas under pressure to pressurize the substantially enclosed gas pressurization chamber, and a gas outlet orifice in the curved face extent configured so that a laminar gas flow at a pressure greater than ambient pressure flows from the substantially enclosed gas pressurization chamber in directions normal to the gas outlet orifice, and
   a liquid conduit including a liquid outlet orifice located below the gas outlet orifice and above the surface, configured to provide a layer of liquid through the liquid outlet orifice below the laminar gas flow so that the laminar gas flow propels the layer of liquid in a laminar flow across the surface,
   wherein the gas outlet orifice comprises a slit in the curved face extent, the slit having parallel top and bottom extents spaced apart at least substantially vertically, the top and bottom extents being substantially parallel to the surface and defining directions normal to the slit that are at least substantially parallel to the surface so that the laminar gas flow is at least substantially parallel to the surface, and the slit having an at least substantially uniform height, the height of the slit being the dimension of the slit between the top and bottom extents measured in a direction perpendicular to the surface, and
   wherein the substantially enclosed gas pressurization chamber comprises a ceiling, a floor and at least one wall connecting the ceiling and floor, the substantially enclosed gas pressurization chamber having a height defined by the height of the at least one wall, and the slit has a height of from about 5% to about 20% of the height of the substantially enclosed gas pressurization chamber.

2. The apparatus of claim 1 comprised in a self cleaning dental mirror tool, wherein
   the surface is a reflective mirror surface;
   the liquid outlet orifice is disposed proximate to one edge of the reflective mirror surface for dispensing a thin layer of a liquid onto the reflective mirror surface; and
   the gas outlet orifice is disposed above the liquid outlet orifice for simultaneously dispensing a thin laminar flow of gas across and parallel to the reflective mirror surface at a pressure greater than that of the layer of liquid.

3. The apparatus of claim 2, further comprising a handle attached to the reflective mirror surface, wherein the gas conduit and the liquid conduit are located in the handle.

4. The apparatus of claim 1, wherein the directions normal to the slit are sufficiently divergent so that the laminar gas flow flows across at least substantially the entirety of the surface.

5. The apparatus of claim 1 wherein the laminar gas flow from the gas outlet orifice is substantially unobstructed.

6. The apparatus of claim 1 wherein the substantially enclosed gas pressurization chamber is generally the shape of a horizontal cylinder segment and the slit extends along about 90 to 120 degrees of the circumference of the substantially enclosed gas pressurization chamber.

7. The apparatus of claim 1 wherein the gas outlet orifice comprises two slits.

8. A method for preventing and removing contaminants from a surface comprising:
   providing a substantially enclosed gas pressurization chamber with a curved face extent,
   providing a gas inlet orifice in the substantially enclosed gas pressurization chamber,
   flowing gas under pressure through the gas inlet orifice into the substantially enclosed gas pressurization chamber to pressurize the substantially enclosed gas pressurization chamber,
   providing a gas outlet orifice in the curved face extent so that a pressurized, laminar flow of gas flows from the substantially enclosed gas pressurization chamber in directions normal to the gas outlet orifice;
   providing a liquid conduit including a liquid outlet orifice downstream of the gas outlet orifice; and
   flowing a liquid from the liquid conduit through the liquid outlet orifice onto the surface so that the pressurized laminar flow of gas propels the liquid in a laminar liquid flow across the surface;
   wherein the gas outlet orifice comprises a slit in the curved face extent, the slit having parallel top and bottom extents spaced apart at least substantially vertically, the to and bottom extents being substantially parallel to the surface and defining directions normal to the slit that are at least substantially parallel to the surface so that the pressurized laminar flow of gas is at least substantially parallel to the surface, and the slit having an at least substantially uniform height, the height of the slit being the dimension of the slit between the top and bottom extents measured in a direction perpendicular to the surface, and wherein the substantially enclosed gas pressurization chamber comprises a ceiling, a floor and at least one wall connecting the ceiling and floor, the substantially enclosed gas pressurization chamber having a height defined by the height of the at least one wall, and the slit has a height of from about 5% to about 20% of the height of the substantially enclosed gas pressurization chamber.

9. The method of claim 8, wherein the liquid is water.

10. The method of claim 8, wherein the gas is air.

11. The method of claim 8, further comprising mixing a surface tension reducer into the flow of liquid upstream of the liquid outlet orifice.

12. The method of claim 11, wherein said mixing comprises placing a cartridge of surface tension reducer in water-soluble resin form in-line with the liquid conduit so that the surface tension reducer is dissolved into the flow of liquid at a generally metered rate.

13. The method of claim 8 wherein the pressurized laminar flow of gas from the gas outlet orifice is substantially unobstructed.

* * * * *

UNITED STATES PATENT AND TRADEMARK OFFICE
CERTIFICATE OF CORRECTION

| | | |
|---|---|---|
| PATENT NO. | : 8,282,393 B2 | Page 1 of 1 |
| APPLICATION NO. | : 12/798595 | |
| DATED | : October 9, 2012 | |
| INVENTOR(S) | : Rany Miles Widen | |

It is certified that error appears in the above-identified patent and that said Letters Patent is hereby corrected as shown below:

Col. 2, line 59, "to and bottom" should be --top and bottom--

Signed and Sealed this
Eighteenth Day of December, 2012

David J. Kappos
*Director of the United States Patent and Trademark Office*